(12) United States Patent
Kelly

(10) Patent No.: US 10,905,862 B2
(45) Date of Patent: Feb. 2, 2021

(54) DRUG DELIVERY BALLOON APPARATUS AND METHODS FOR USE

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 127 days.

(21) Appl. No.: 16/364,288

(22) Filed: Mar. 26, 2019

(65) Prior Publication Data
US 2019/0217066 A1 Jul. 18, 2019

Related U.S. Application Data

(63) Continuation of application No. 15/458,783, filed on Mar. 14, 2017, now Pat. No. 10,258,775, which is a (Continued)

(51) Int. Cl.
*A61M 25/10* (2013.01)
*A61M 25/09* (2006.01)
*A61M 39/24* (2006.01)

(52) U.S. Cl.
CPC ........ *A61M 25/1025* (2013.01); *A61M 25/09* (2013.01); *A61M 25/1002* (2013.01);
(Continued)

(58) Field of Classification Search
CPC ........ A61M 25/1002; A61M 2025/105; A61M 2025/1052; A61M 2025/1056;
(Continued)

(56) References Cited

U.S. PATENT DOCUMENTS 5,045,061 A 9/1991 Seifert
5,207,648 A * 5/1993 Gross ................ A61M 25/0014
604/164.09
(Continued)

FOREIGN PATENT DOCUMENTS

EP 2495007 9/2012
JP 200611256 A 4/2006
(Continued)

OTHER PUBLICATIONS

International Search Reporting for corresponding PCT application No. PCT/US2014/032964, dated Sep. 12, 2014*.
(Continued)

*Primary Examiner* — Jason E Flick
(74) *Attorney, Agent, or Firm* — McDonnell Boehnen Hulbert & Berghoff LLP

(57) ABSTRACT

A drug delivery balloon apparatus is disclosed herein, comprising: (a) at least two lumens, comprising a first lumen and a second lumen, (b) a balloon inflation port in fluid communication with the first lumen, (c) a drug delivery port in fluid communication with the second lumen, (d) a guidewire port in fluid communication with the second lumen, wherein the second lumen is configured to receive both a guidewire and a drug solution, (e) an occlusion balloon, (f) a drug delivery balloon, where the occlusion balloon and the drug delivery balloon are in fluid communication with the first lumen, (g) one or more drug delivery channels extending the length of the second lumen, and (h) one or more drug delivery ducts extending from the one or more drug delivery channels to an exterior surface of the second lumen.

21 Claims, 4 Drawing Sheets

Related U.S. Application Data continuation of application No. 14/244,126, filed on Apr. 3, 2014, now Pat. No. 9,629,985.

(60) Provisional application No. 61/809,176, filed on Apr. 5, 2013.

(52) U.S. Cl.
CPC ........ A61M 25/1011 (2013.01); A61M 39/24 (2013.01); *A61M 2025/105* (2013.01); *A61M 2025/1052* (2013.01); *A61M 2025/1056* (2013.01); *A61M 2025/1086* (2013.01)

(58) Field of Classification Search
CPC .......... A61M 2025/1086; A61M 25/09; A61M 25/1011; A61M 25/1025; A61M 39/24; A61M 2025/0059; A61M 25/104; A61M 25/10; A61M 2025/1004; A61M 2025/1043; A61M 2025/1061
See application file for complete search history.

(56) References Cited

U.S. PATENT DOCUMENTS

| | | | |
|---|---|---|---|
| 5,295,959 A | 3/1994 | Gurbei | |
| 5,545,132 A * | 8/1996 | Fagan | A61M 25/1002 604/103.08 |
| 5,704,361 A * | 1/1998 | Seward | A61B 8/06 128/916 |
| 6,623,452 B2 | 9/2003 | Chien | |
| 6,685,672 B1 * | 2/2004 | Forman | A61M 25/1011 604/101.03 |
| 8,182,446 B2 * | 5/2012 | Schaeffer | A61M 25/10 604/101.05 |
| 2007/0088317 A1 * | 4/2007 | Hyde | A61B 17/22 604/500 |
| 2007/0197963 A1 * | 8/2007 | Griffiths | A61M 5/007 604/97.01 |
| 2011/0152683 A1 | 6/2011 | Gerrans | |
| 2012/0316436 A1 | 12/2012 | Lentz | |

FOREIGN PATENT DOCUMENTS

| | | |
|---|---|---|
| JP | 2006511256 A | 4/2006 |
| JP | 2010158483 A | 7/2010 |
| WO | 2009076732 A1 | 6/2009 |

OTHER PUBLICATIONS

English translation of Japanese office action for corresponding Japanese application No. 2016-506643, dated Jul. 10, 2018*.

* cited by examiner

DRUG DELIVERY BALLOON APPARATUS AND METHODS FOR USE

CROSS-REFERENCE TO RELATED APPLICATIONS

This application is a continuation of U.S. Non-Provisional application Ser. No. 15/458,783 entitled "Drug Delivery Balloon Apparatus and Methods for Use", filed on Mar. 14, 2017, which is a continuation of U.S. Non-Provisional application Ser. No. 14/244,126 entitled "Drug Delivery Balloon Apparatus and Methods for Use", filed on Apr. 3, 2014, which claims the benefit of the filing date of U.S. Provisional Application No. 61/809,176 entitled "Drug Delivery Balloon Apparatus & Methods for Use," filed on Apr. 5, 2013, the contents of each of which are hereby incorporated by reference in their entirety.

BACKGROUND OF THE INVENTION

Local drug delivery is the process by which therapeutic agents are delivered to specific areas within the vasculature of a human or animal patient. This localized treatment permits an increased concentration of the drug or therapeutic agent at the intended target area but avoids toxicity that may result through general systemic delivery within the circulatory system. Known localized drug delivery methods include drug-eluting stents or balloons, porous drug infusion balloons and direct catheter delivery.

SUMMARY OF THE INVENTION

The present invention is directed to methods and apparatus for the delivery of a drug solution or a therapeutic agent to a selected site within the vascular system using a drug delivery balloon apparatus. The drug delivery balloon apparatus of the present invention may beneficially permit an increased balloon length that may be up to four times longer than that of other known balloons providing the advantage of treating larger injury sites in a single procedure. The drug delivery balloon apparatus of the present invention may also provide a plurality of grooves for receiving the drug solution during delivery to the target passage. These grooves may beneficially guide the flow of the drug solution through the target passage, while at the same time slowing the drug flow to increase the amount of time that the drug is in contact with the wall of the target passage. The drug delivery balloon apparatus and its associated channels also can help to minimize the volume of drug solution required by occupying a portion of the luminal volume. In addition, the drug delivery balloon apparatus may further include an occlusion balloon that may inflate upstream from the drug delivery balloon to permit adequate pressure to be maintained in the system during infusion to effectively advance the drug or therapeutic agent into and along the plurality of grooves on the outer surface of the drug delivery balloon. The occlusion balloon also helps to prevent peripheral washout by blocking blood flow from the treatment area.

Thus, in a first aspect, the present invention provides a drug delivery balloon apparatus comprising: (a) at least two lumens, comprising a first lumen and a second lumen, (b) a balloon inflation port in communication with the first lumen, (c) a drug delivery port in communication with the second lumen, (d) a guidewire port in communication with either the second lumen or a third lumen, (e) an occlusion balloon, (f) a drug delivery balloon, wherein an outer surface of the drug delivery balloon defines a plurality of grooves extending from a first end of the drug delivery balloon to a second end of the drug delivery balloon, wherein the occlusion balloon is disposed between the drug delivery balloon and the balloon inflation port, wherein the occlusion balloon and the drug delivery balloon are in communication with the first lumen, (g) one or more drug delivery channels extending the length of the second lumen, (h) one or more drug delivery ducts extending from the one or more drug delivery channels to an exterior surface of the second lumen, and wherein the one or more drug delivery ducts are defined only in a portion of the second lumen that is disposed between the occlusion balloon and the drug delivery balloon.

In one embodiment, the invention provides that the plurality of grooves may be axially aligned with a central axis of the drug delivery balloon. In various other embodiments, the plurality of grooves may be spiraled, helical, substantially straight, sinusoidal, or cross-hatched, for example. Further, in one example, the drug delivery port may be branched such that two, three, four or more different drug solutions or other solutions may be introduced into the drug delivery port. In another embodiment, the invention may provide that the one or more drug delivery channels comprises four channels and each drug delivery channel may be in communication with three drug delivery ducts such that there are a total of twelve drug delivery ducts.

In a second aspect, the present invention also provides a method for administering at least one drug to a subject in need thereof using a drug delivery balloon apparatus, the method comprising: (a) introducing the drug delivery balloon apparatus according to the first aspect of the invention to a target passage, (b) inflating the occlusion balloon and the drug delivery balloon, (c) injecting a drug solution into the drug delivery port, and (d) advancing the drug solution through the second lumen to the one or more drug delivery ducts into the target passage in the subject and then into and along a plurality of grooves defined in an outer surface of the drug delivery balloon.

DETAILED DESCRIPTION OF THE INVENTION

Figure 1A:
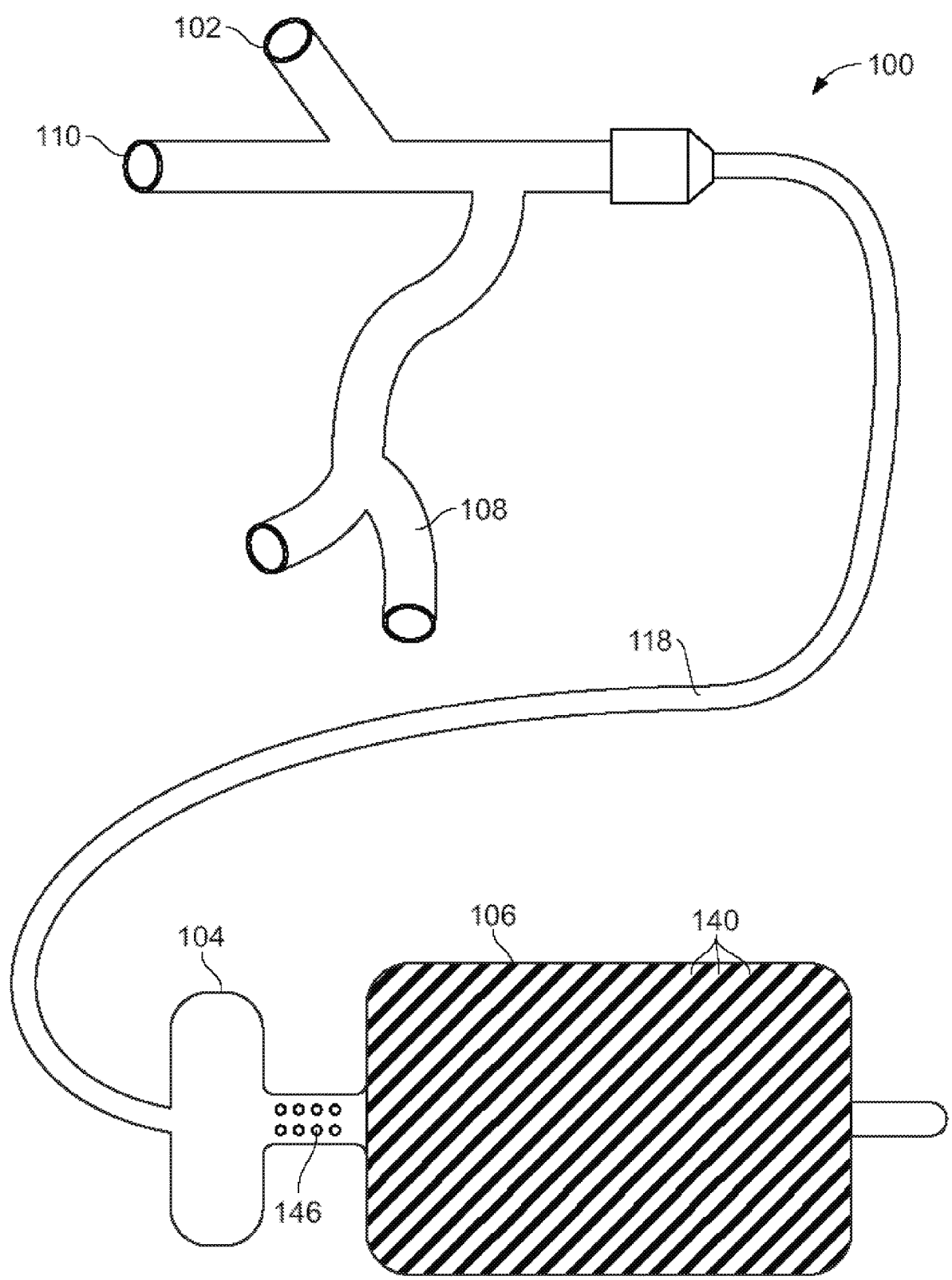
FIG. 1A is a side view of drug delivery balloon apparatus, in accordance with one embodiment of the invention.

Exemplary methods and systems are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means+/−5%. Further, as used herein, "target passage" refers to the blood vessel or artery in which the drug delivery balloon is deployed to effectively administer a drug solution. The target passage may further include artificial lumens used, for example, as teaching aids.

In addition, as used herein, "drug solution" refers to any flowable material that may be administered into a target passage. When the drug solution comprises a therapeutic to be administered to a subject, any suitable drug that can be administered in solution can be used. In various non-limiting embodiments, the therapeutic may comprise sirolimus, heparin, and cell-based therapies; and antineoplastic, anti-inflammatory, antiplatelet, anticoagulant, antifibrin, anti-thrombin, antimitotic, antibiotic, antiallergic and antioxidant substances. Examples of such antineoplastics and/or antimi-totics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin. In addition, non-therapeutic fluids, such as water, may be used, if the drug delivery balloon apparatus is being used in a teaching model or training demonstration, for example.

In a first aspect, FIG. 1A illustrates an example drug delivery balloon apparatus 100 in accordance with one embodiment of the invention. The drug delivery balloon apparatus 100 may include three ports: (1) a balloon inflation port 102 that inflates both an occlusion balloon 104 and a drug delivery balloon 106, (2) a drug delivery port 108 through which a drug solution is administered, and (3) a guidewire port 110 for receiving a guidewire and the inflated occlusion balloon 104 and drug delivery balloon 106. In one example embodiment as shown in FIG. 1A, the drug delivery port 108 may be bifurcated, such that two, three, four or more different drug solutions or other solutions may be introduced into the drug delivery port 108 as deemed appropriate for treatment.

Figure 1B:
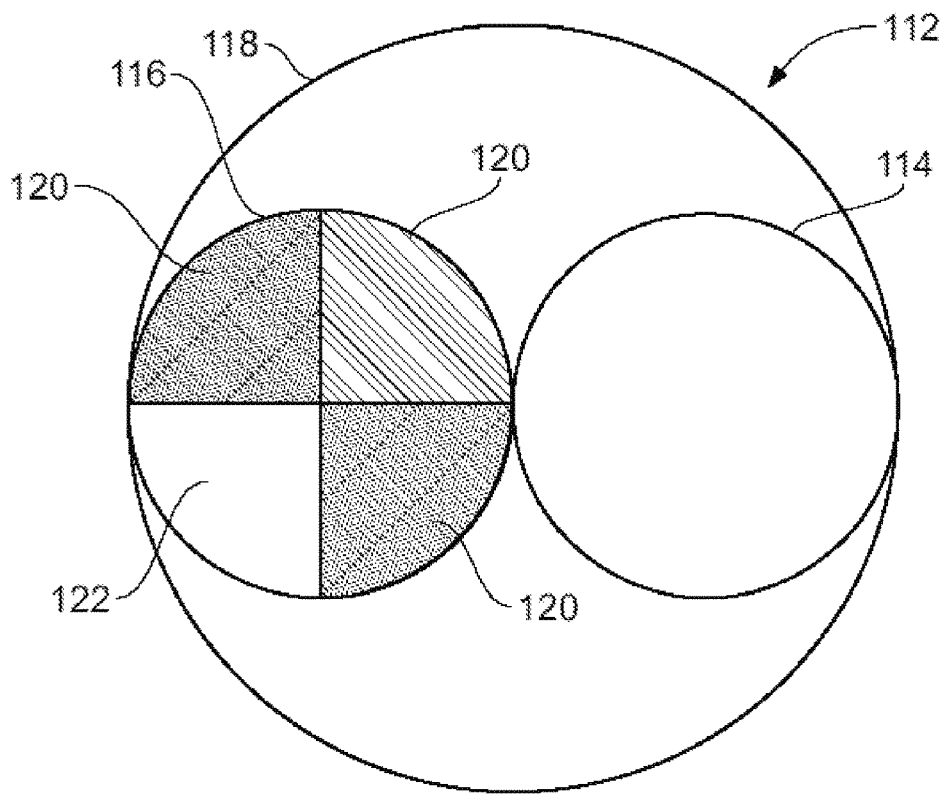
FIG. 1B is a front cross-sectional view of a two lumen configuration of the drug delivery balloon apparatus, in accordance with one embodiment of the invention.

In one example, the three ports lead to two parallel lumens 112. FIG. 1B illustrates a front cross-sectional view of the two lumens. The balloon apparatus 100 may include a first lumen 114 in communication with the balloon inflation port 102 and may be configured to receive a saline contrast mixture, or any other suitable fluid medium, to inflate the occlusion balloon 104 and the drug delivery balloon 106. Further, the balloon apparatus 100 may include a second lumen 116 in communication with the drug delivery port 108 and the guidewire port 110. In one embodiment, the second lumen 116 may be sized and shaped to receive a drug solution. In one embodiment, the second lumen 116 may also be sized and shaped to receive a guidewire having a diameter in the range from about 0.25 mm to about 1 mm, and preferably in a range from about 0.254 mm to about 0.9652 mm. In one embodiment, the first lumen 114 and the second lumen 116 may be enclosed in a sheath 118. The second lumen 116 may include one or more drug delivery channels 120 extending the length of the second lumen 116. These drug delivery channels 120 may be used to transport the drug solution from the drug delivery port 108 to a target passage. The second lumen 116 may also include a guidewire channel 122 extending the length of the second lumen 116. In another example, the second lumen 116 may include a single channel for both the guidewire and drug solution.

In such a configuration, the guidewire may be removed after use so that the drug solution can pass through the second lumen 116. In operation, the balloon apparatus 100 may be configured to infuse the drug solution while the guidewire is in the second lumen 116. In such a configuration, the second lumen 116 would have a larger diameter than the guidewire from a location between the guidewire port 110 and the drug delivery port 108 until just distal to the drug delivery ducts 146. The second lumen 116 would shrink down to about the diameter of the guidewire just distal to the drug delivery ducts 146 to the distal end of the balloon. Further, the second lumen 116 would shrink down to about the diameter of the guidewire proximal to the drug delivery port 108, so as to prevent the drug solution from exiting the guidewire port 110. In another example, a flange or one-way valve may be used to prevent the drug solution from exiting the guidewire port 110. Other configurations are possible as well.

Figure 1C:
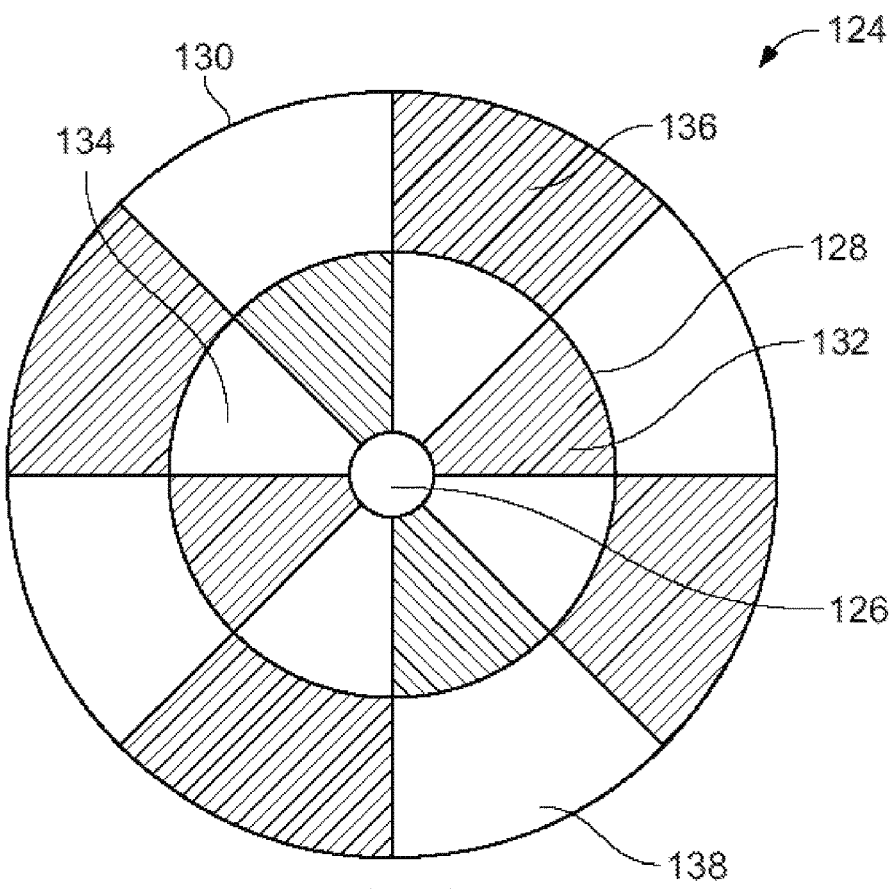
FIG. 1C is a front cross-sectional view of a three lumen configuration of the drug delivery balloon apparatus, in accordance with one embodiment of the invention.

In another embodiment, the three ports may be coupled to three concentrically aligned lumens 124. For example, FIG. 1C illustrates a front cross-sectional view of the three lumens 124. As shown in FIG. 1C, the three concentrically aligned lumens 124 comprise an inner lumen 126, a middle lumen 128, and an outer lumen 130, where the first lumen is arranged as the inner lumen, the second lumen is arranged as the middle lumen and the third lumen is arranged as the outer lumen. The inner lumen 126 may be in communication with the guidewire port 110 and may be sized and shaped to receive a guidewire having a diameter in the range from about 0.25 mm to about 1 mm, and preferably in a range from about 0.254 mm to about 0.9652 mm. The middle lumen 128 may be in communication with the drug delivery port 108. The middle lumen 128 may include a plurality of flexible spacers 132 that extend between the inner lumen 126 and the outer lumen 130 to maintain the structural integrity of the middle lumen 128. These spacers 132, in combination with the middle lumen 128 and the inner lumen 126, may further define one or more drug delivery channels 134 extending the length of the middle lumen 128. As discussed above, these drug delivery channels 134 may be used to transport the drug solution from the drug delivery port 108 to a target passage. The outer lumen 130 may be in communication with the balloon inflation port 102. The outer lumen 130 may also include a plurality of flexible spacers 136 to help maintain the structural integrity of the outer lumen 130. These spacers 136, in combination with the outer lumen 130 and middle lumen 128, may also define a plurality of fluid delivery channels 138 extending the length of the outer lumen 130. These fluid delivery channels 138 may be in fluid communication with the occlusion balloon 104 and the drug delivery balloon 106.

Figure 1D:
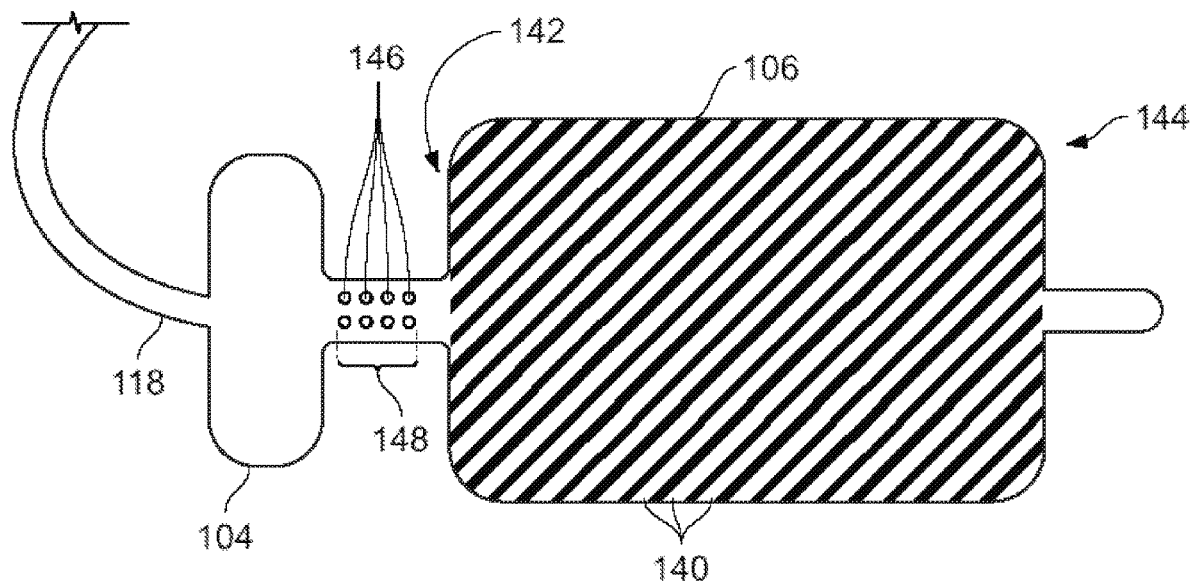
FIG. 1D is a side view of the occlusion balloon and the drug delivery balloon of the drug delivery balloon apparatus, in accordance with one embodiment of the invention.

FIG. 1D illustrates the occlusion balloon 104 and the drug delivery balloon 106 of the drug delivery balloon apparatus 100. The occlusion balloon 104 may be composed of atraumatic compliant materials such as polyurethane, latex, or silicone, among other possibilities, that results in a low burst pressure of about 5 atm, for example. However, the occlusion balloon 104 may be configured to withstand greater pressures, for example up to about 20 atm. The occlusion balloon 104 may be configured to conform to the shape and size of the target passage via low pressure inflation, about 1 to 2 atm. Once inflated, the occlusion balloon 104 may provide occlusion in the target passage to allow for drug delivery into the target passage downstream from the occlusion balloon 104 to minimize dilution of the drug solution from blood flow. The inflated diameter of the occlusion balloon 104 may range from about 2.5 mm to about 12 mm and is preferably in a range from about 2.5 mm to about 6 mm. The length of the occlusion balloon 104 may range from about 20 mm to about 40 mm. In one embodiment, the inflated diameter of the occlusion balloon 104 ranges from about the same as the inflated diameter of the drug delivery balloon 106 to about 2 mm larger than the inflated diameter of the drug delivery balloon 106. In operation, the occlusion balloon 104 may be inflated prior to the introduction of the drug solution into the drug delivery port 108.

The drug delivery balloon 106 may be made of compliant materials such as polyurethane, latex, or silicone that results in a low burst pressure of about 5 atm, for example. The length of the drug delivery balloon 106 may range from about 20 mm to about 200 mm. In various embodiments, the length of the drug delivery balloon 106 ranges from about 80 mm to about 200 mm, from about 100 mm to about 200 mm, from about 120 mm to about 200 mm, from about 140 mm to about 200 mm, from about 160 mm to about 200 mm, from about 180 mm to about 200 mm, from about 60 mm to about 120 mm, from about 60 mm to about 100 mm, and from about 10 mm to about 80 mm. In one embodiment, the drug delivery balloon 106 may have an inflated diameter ranging from about 2.5 mm to about 12 mm and is preferably in a range from about 2.5 mm to about 6 mm. In various embodiments, the inflated diameter of the drug delivery balloon 106 may range from about 2.5 mm to about 3 mm, from about 4 mm to about 5 mm, and from about 5 mm to about 6 mm.

The outer surface of the drug delivery balloon 106 may define a plurality of grooves 140 for receiving the drug solution. These grooves 140 may extend from the first end 142 to the second end 144 of the drug delivery balloon 106. The plurality of grooves 140 may serve to (1) guide the flow of the drug solution and (2) slow the flow of the drug solution to increase the time of contact of the drug with the wall of the target passage. The plurality of grooves 140 are preferably axially aligned with a central axis of the drug delivery balloon 106 and may be spiraled, helical, sinusoidal or substantially straight, among other possibilities, in various embodiments. Spiraled, helical or sinusoidal grooves are preferred over straight grooves, because the more tortuous grooves provide more surface area to contact the vessel wall and further extend the amount of time that the drug solution contacts the vessel wall. Further, any pattern of grooves is contemplated including a cross-hatched or waffle pattern, for example.

The occlusion balloon 104 may be disposed between the drug delivery balloon 106 and the balloon inflation port 102 such that both the occlusion balloon 104 and the drug delivery balloon 106 may be in communication with the second lumen 116 or the outer lumen 130 and receive fluid from the balloon inflation port 102. The occlusion balloon 104 and the drug delivery balloon 106 may be separated from each other by a distance ranging from about 1 mm to about 10 mm, and preferably from about 3 mm to about 5 mm. This distance allows adequate pressure to be maintained in the system such that the drug solution may be effectively advanced into and along the plurality of grooves 140 on the outer surface of the drug delivery balloon 106.

One or more drug delivery ducts 146 may extend from the one or more drug delivery channels 120 defined in the second lumen 116 to an exterior surface of the second lumen 116. These drug delivery ducts 146 may be defined in a portion 148 of the second lumen 116 that is disposed between the occlusion balloon 104 and the drug delivery balloon 106. In other words, these drug delivery ducts 130 may be downstream from the occlusion balloon 104 in operation. In one embodiment, the one or more drug delivery channels 120 may comprise four to eight channels. In another embodiment, the one or more drug delivery channels 120 is each in fluid communication with one to six drug delivery ducts 146. In a further embodiment, the one or more drug delivery channels 120 may comprise four channels and each drug delivery channel may be in fluid communication with three drug delivery ducts such that there are a total of twelve drug delivery ducts. The number of drug delivery ducts may depend upon the length of portion 148 of the second lumen 116 extending between the occlusion balloon 104 and the drug delivery balloon 106 and/or the diameter of the drug delivery ducts 146, among other possibilities.

Figure 1E:
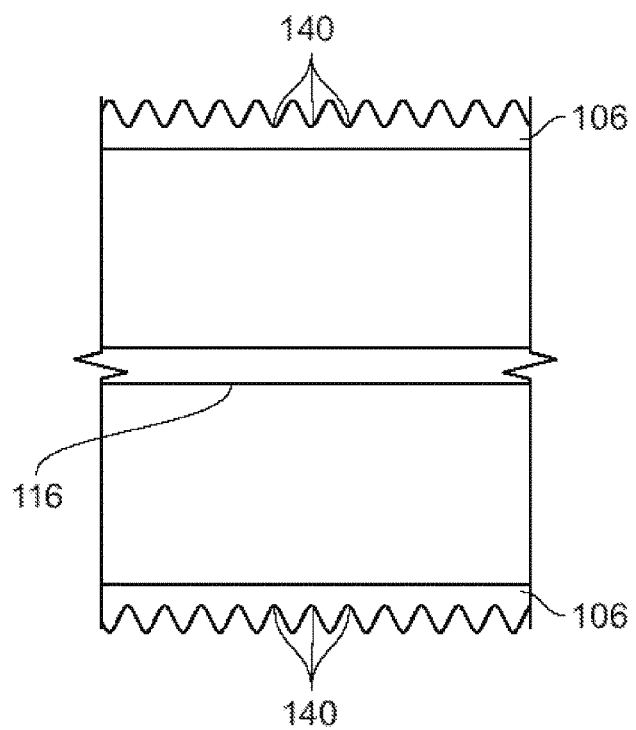
FIG. 1E is a detail cross-sectional side view of the drug delivery balloon, in accordance with one embodiment of the invention.

FIG. 1E illustrates a cross-sectional side view of the drug delivery balloon 106. As shown in FIG. 1E, the drug delivery balloon 106 includes a plurality of grooves 140. In operation, the drug solution advances downstream into and along the plurality of grooves 140 defined in the outer surface of the drug delivery balloon 106. Once the drug solution exits the plurality of grooves 140 at the second end 144 of the drug delivery balloon 106, the drug solution may be cleared via normal arterial blood flow and ultimate physiological function.

Figure 2:
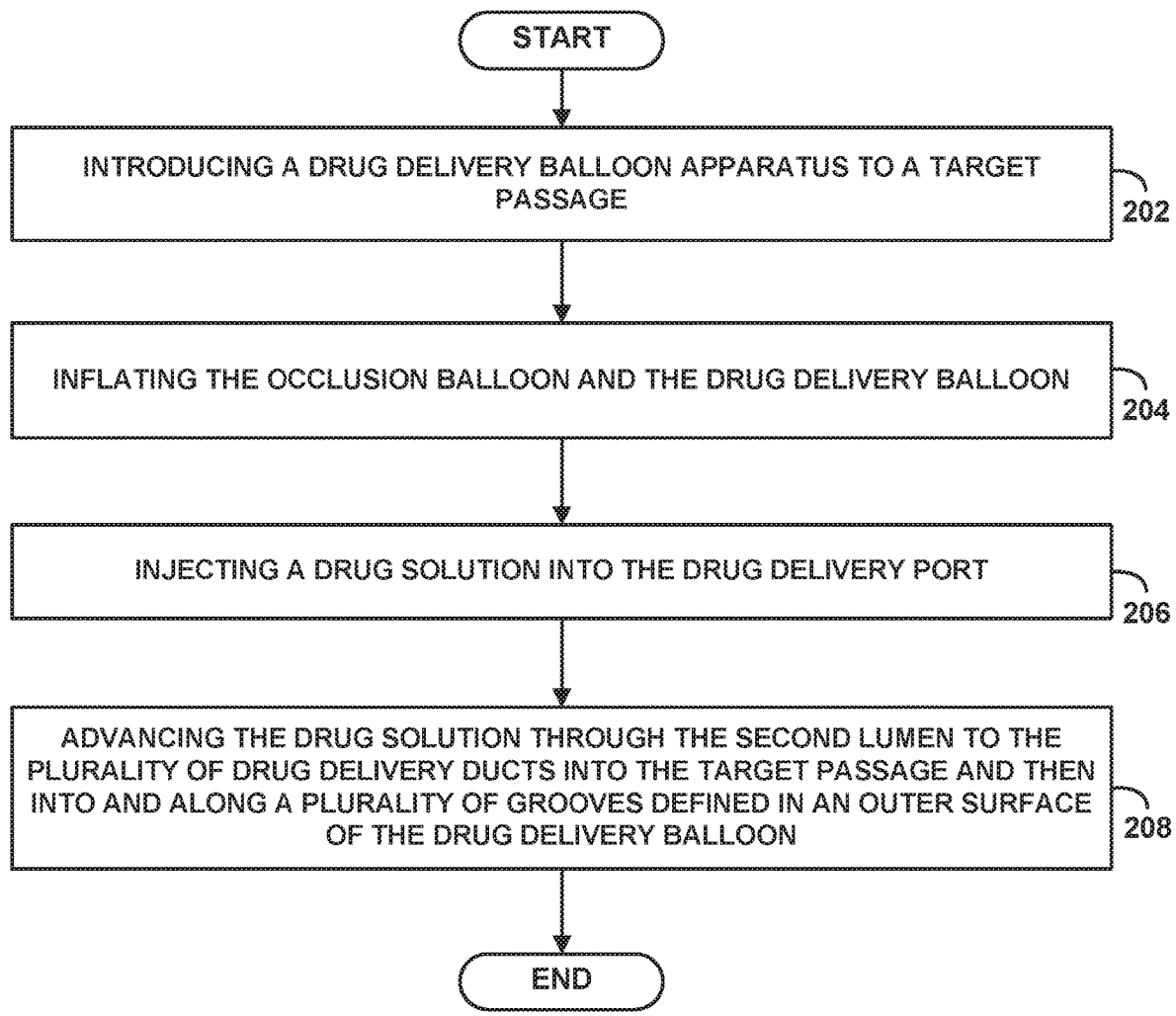
FIG. 2 is a flow chart depicting functions that can be carried out in accordance with example embodiments of the disclosed methods.

FIG. 2 is a simplified flow chart illustrating a method according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 202, the method involves introducing the drug delivery balloon apparatus according to any of the foregoing embodiments to a target passage. The drug delivery balloon apparatus may be introduced and delivered in a standard coaxial manner, via over-the-wire or rapid exchange techniques, as examples.

At block 204, the method involves inflating the occlusion balloon and the drug delivery balloon. In one embodiment, the occlusion balloon and the drug delivery balloon may be inflated by injecting a saline contrast mixture, for example, into the balloon inflation port. The saline contrast mixture may then be advanced through a first lumen to the occlusion balloon and the drug delivery balloon until both balloons are inflated. The occlusion balloon may inflate at a slightly faster rate, since the occlusion balloon and the drug delivery balloon are connected in series such that the occlusion balloon receives the saline contrast inflation mixture first. In another embodiment, the occlusion balloon and drug delivery balloon may be inflated using any other suitable fluid medium.

After both the occlusion balloon and the drug delivery balloon have been inflated, the method continues at block 206 with injecting a drug solution into the drug delivery port. In one embodiment, the drug delivery port is bifurcated, such that two, three, four or more different drug solutions or other solutions may be introduced into the drug delivery port as deemed appropriate.

At block 208, the method involves advancing the drug solution through a second lumen to the one or more drug delivery ducts into a target passage in the subject. At this stage, the space between the occlusion balloon and the drug delivery balloon acts as a reservoir storing the drug solution as it is delivered via the drug delivery ducts. Due to the pressure at which the drug solution is being introduced to the drug delivery port, the drug solution advances downstream into and along the plurality of grooves defined in the outer surface of the drug delivery balloon. The pressure at which the drug solution is administered should not exceed about 2 atm. Once the drug solution exits the plurality of grooves at the second end of the drug delivery balloon, the drug solution may be cleared via normal arterial blood flow and ultimate physiological function.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the following claims.

The invention claimed is:

1. A drug delivery balloon apparatus comprising:
at least three lumens, comprising a first lumen, a second lumen, and a third lumen;
a balloon inflation port in fluid communication with the first lumen;
a drug delivery port in fluid communication with the second lumen;
a guidewire port in fluid communication with the third lumen;
an occlusion balloon;
a drug delivery balloon, wherein an outer surface of the drug delivery balloon defines a plurality of grooves extending from a first end of the drug delivery balloon to a second end of the drug delivery balloon, wherein the occlusion balloon is disposed between the drug delivery balloon and the balloon inflation port, wherein the occlusion balloon and the drug delivery balloon are in fluid communication with the first lumen;
one or more drug delivery channels extending a length of the second lumen; and
one or more drug delivery ducts extending from the one or more drug delivery channels to an exterior surface of the second lumen, and wherein the one or more drug delivery ducts are defined only in a portion of the second lumen that is disposed between the occlusion balloon and the drug delivery balloon.

2. The drug delivery balloon apparatus of claim 1, wherein the first lumen, the second lumen and the third lumen are concentrically aligned such that the third lumen is arranged as an inner lumen, the second lumen is arranged as a middle lumen, and the first lumen is arranged as an outer lumen.

3. The drug delivery balloon apparatus of claim 2, further comprising:
a first plurality of spacers extending between the inner lumen and the outer lumen configured to maintain a structural integrity of the middle lumen, wherein the first plurality of spacers in combination with the middle lumen and the inner lumen define the one or more drug delivery channels extending the length of the second lumen.

4. The drug delivery balloon apparatus of claim 3, wherein the outer lumen includes a second plurality of spacers configured to maintain a structural integrity of the outer lumen, wherein the second plurality of spacers in combination with the outer lumen and the middle lumen define a plurality of fluid delivery channels extending a length of the outer lumen.

5. The drug delivery balloon apparatus of claim 1, wherein the plurality of grooves are axially aligned with a central axis of the drug delivery balloon.

6. The drug delivery balloon apparatus of claim 1, wherein the plurality of grooves are spiraled, helical, substantially straight, sinusoidal, or cross-hatched.

7. The drug delivery balloon apparatus of claim 1, wherein the occlusion balloon and the drug delivery balloon are separated from each other by a distance ranging from about 3 mm to about 5 mm.

8. The drug delivery balloon apparatus of claim 1, wherein the drug delivery port is bifurcated.

9. The drug delivery balloon apparatus of claim 1, wherein the occlusion balloon and the drug delivery balloon each have an inflated diameter ranging from about 2.5 mm to about 12 mm.

10. The drug delivery balloon apparatus of claim 9, wherein the inflated diameter of the occlusion balloon ranges from about the same as the inflated diameter of the drug delivery balloon to about 2 mm larger than the inflated diameter of the drug delivery balloon.

11. The drug delivery balloon apparatus of claim 1, wherein the occlusion balloon ranges in length from about 20 mm to about 40 mm.

12. The drug delivery balloon apparatus of claim 1, wherein the drug delivery balloon ranges in length from about 50 mm to about 200 mm.

13. The drug delivery balloon apparatus of claim 1, wherein the drug delivery balloon is about 200 mm in length.

14. The drug delivery balloon apparatus of claim 1, wherein the guidewire port is sized to receive a guidewire, and wherein the guidewire has a diameter ranging from about 0.25 mm to about 1 mm.

15. The drug delivery balloon apparatus of claim 1, wherein the one or more drug delivery channels comprises four to eight channels.

16. The drug delivery balloon apparatus of claim 1, wherein the one or more drug delivery channels is each in fluid communication with one to six drug delivery ducts of the one or more drug delivery ducts.

17. The drug delivery balloon apparatus of claim 1, wherein the one or more drug delivery channels comprises four channels and each drug delivery channel is in fluid communication with three drug delivery ducts such that there are a total of twelve drug delivery ducts.

18. A method for administering at least one drug to a subject in need thereof using a drug delivery balloon apparatus, the method comprising:
   introducing the drug delivery balloon apparatus of claim 1 into a target passage;
   inflating the occlusion balloon and the drug delivery balloon;
   injecting a drug solution into the drug delivery port; and
   advancing the drug solution through the second lumen to the one or more drug delivery ducts into the target passage in the subject and then into and along the plurality of grooves defined in an outer surface of the drug delivery balloon.

19. The method of claim 18, wherein injecting the drug solution is performed at a fluid pressure at or below 2 atm.

20. The method of claim 18, wherein an inflated diameter of the occlusion balloon ranges from about the same as the inflated diameter of the drug delivery balloon to about 2 mm larger than the inflated diameter of the drug delivery balloon.

21. The method of claim 18, wherein inflating the occlusion balloon and the drug delivery balloon comprises:
   injecting a saline contrast mixture into the balloon inflation port; and
   advancing the saline contrast mixture through the first lumen to the occlusion balloon and the drug delivery balloon.

\* \* \* \* \*